(12) United States Patent
Igarashi et al.

(10) Patent No.: US 6,423,838 B1
(45) Date of Patent: Jul. 23, 2002

(54) GENE FOR PROLINE TRANSPORTER IN RICE

(75) Inventors: Yumiko Igarashi, Kawagoe; Yoshu Yoshiba, Ageo, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/637,118

(22) Filed: Aug. 11, 2000

(30) Foreign Application Priority Data

Aug. 17, 1999 (JP) ............................................. 11-230291

(51) Int. Cl.[7] .......................... C12N 15/10; C12N 15/11; C12N 15/29; C12N 15/82; C12N 15/83
(52) U.S. Cl. .................... 536/23.6; 536/24.3; 536/23.2; 435/320.1; 435/6
(58) Field of Search .............................. 536/24.3, 23.6, 536/23.2; 435/6, 320.1

(56) References Cited

U.S. PATENT DOCUMENTS 6,165,792 A * 12/2000 Allen et al. ................. 435/419

FOREIGN PATENT DOCUMENTS

JP          10-57069         2/2001

OTHER PUBLICATIONS

Yamamoto et al, 1998, GenBank Accession No. AU032560.*

R. Schwacke et al, LeProT1, a transporter for proline, Glycine Betaine, and γ–Amino Butyric Acid in Tomato Pollen, See whole document, especially Results, 3rd and 4th paragraphs; The Plant Cell, vol. 11, pp. 377–391 (Mar. 1999).

Zhang et al, Characterization of $\Delta^1$–pyrroline–5–carboxylate synthetase gene promoter in transgenic *Arabidopsis thaliana* subjected to water, Plant Science, 1997, whole document, especially Results and Discussion, and figs 1, 3, 4; Plant Science, 129 (1997) pp. 81–89.

D. Rentsch et al, Salt Stress–Induced Proline Transporters and Salt Stress–Repressed Broad Specificity Amino Acid Permeases Identified by Suppression of a Yeast Amino Acid Permease–Targeting Mutant; The Plant Cell, vol. 8, pp. 1437–1446 (Aug. 1996).

Yoshiba et al., "Correlation between the induction of a gene for $\Delta^1$–pyrroline–5–carboxylate synthetase and the accumulation in *Arabidopsis thaliana* under osmotic stress" (Plant J. 1995) vol. 7, pp. 751–760.

Kishor et al., "Overexpression of $\Delta^1$–pyrroline–5–carboxylate synthetase increase proline production and confers osmotolerance in trangenic plants" (Plant Phys. 1995) vol. 108, pp. 1387–1394.

Rentach et al. (Salt stress–induced proline transporters and salt stress–repressed broad specificity amino acid permeases identified by suppression of a yeast amino acid permease–targeting mutant (The Plant Cell 1996) vol. 8, pp. 1437–1446.

Schwacke et al., "LeProT1, a transporter for proline, glycerine betaine, and γ–amino butyric acid in tomato pollen" (The Plant Cell 1999) vol. 11, pp. 377–391.

* cited by examiner

*Primary Examiner*—David T. Fox
*Assistant Examiner*—Anne Kubelik

(57) ABSTRACT

A cDNA library prepared from rice seedlings is subjected to screening using Arabidopisis proline transporter gene cDNA as a probe. The positive clones thus obtained are subcloned and examined for their length through restriction enzyme treatment and 5' and 3' terminal nucleotide sequences to give a rice proline transporter gene cDNA-containing clone. This cDNA is sequenced and, based on the results of homology searching, a rice proline transporter gene is identified which shows high (68%) homology (amino acid level) with the Arabidopsis-derived ones and is very similar in transmembrane domain (hydropathy plot analysis) and expression pattern (Northern analysis) thereto.

6 Claims, 2 Drawing Sheets

EXPRESSION OF RICE PROLINE TRANSPORTER GENE
IN SEVERAL ORGANS AT SEVERAL GROWTH STAGES

EXPRESSION OF RICE PROLINE TRANSPORTER GENE
UNDER DISTILLED WATER

EXPRESSION OF RICE PROLINE TRANSPORTER GENE
UNDER 250mM NaCl

SEQUENCE LISTING

<160> NUMBER OF SEQ ID NOS: 2

<210> SEQ ID NO 1
<211> LENGTH: 1863
<212> TYPE: DNA
<213> ORGANISM: Oryza sativa L.
<220> FEATURE:
<221> NAME/KEY: CDS
<222> LOCATION: 144..1562
<300> PUBLICATION INFORMATION:
<308> DATABASE ACCESSION NUMBER: AB022783
<309> DATABASE ENTRY DATE: 1999-01-25

<400> SEQUENCE: 1

```
gccgcccgct tgccggagct ctctatctat ctctctatct ctatctctat ccctccagat      60
tccctcctcc atcgaatctc tgatatttgg agggagcgac tcgacgcagc atcgcatcgt     120
aaggaaggtc ccctccactg tcg                                             143 atg gat cag cac cag ctc gac gag gag aac cag aga gcc gcg ctc ttc cac   194 tcc tct gcc cca tct tcc tct ttg gga gct gac ggg gag gag gag agg gag   245 act gtg ccg ctg ctg tcc tgc aag atg gcc gac gat aaa tct gac act gtc   296 cag gtc tcc gag gat acg gcg cac cag att agc att gat ccc tgg tat caa   347 gtt gga ttc att ctg aca acc ggg gtg aat agt gca tat gtt ctg gga tat   398 tct gca tca atc atg gtc cct tta ggc tgg att ggt ggg aca tgt ggc ttg   449 att cta gct gct gca ata tcc atg tat gca aat gct ctt ctt gct cac ctt   500 cat gaa gtt ggt ggc aaa cgc cat atc aga tac aga gat ctt gct ggg cac   551 ata tat ggt aga aaa atg tat tcg ctt aca tgg gct ctg caa tat gtt aat   602 cta ttc atg atc aac act ggc ctt atc att tta gct ggt caa gcc ctg aag   653 gca ata tat gta tta ttt agg gac gat gga gtt cta aag cta ccc tac tgc   704 ata gca tta tct ggg ttt gtc tgt gct ctt ttt gcc ttt gga atc cct tat   755 ctg tct gct ctc agg att tgg ttg gga tta tca aca gtt ttc agt ctc atc   806 tat ata atg ata gca ttt gtc atg tcg ctt aga gat ggg att acc aca cct   857 gca aag gat tat act att cct gga tca cat tca gat aga atc ttc act acg   908 ata ggt gct gta gca aac ctt gtg ttc gct tac aac act gga atg ctc cca   959 gaa att caa gca acc ata agg cct cct gtg gtc aag aat atg gag aag gct  1010 cta tgg ttc cag ttc act gtt ggt tcg ttg cct ctt tat gct gtc acc ttt  1061 atg ggg tat tgg gcg tac ggg tcc tca aca tca agc tat cta ctg aat agt  1112 gtg aag gga cca att tgg ata aaa act gtg gca aat tta tcg gcg ttt ctt  1163
```

-continued

```
cag act gtc ata gca tta cat ata ttt gca agc cca atg tac gaa ttc ttg    1214 gac aca aga ttc ggc agt gga cat ggt ggt cct ttt gca atc cac aac ata    1265 atg ttc aga gtg ggt gtc aga gga ggc tac ctg acc gtc aac acc ttg gtg    1316 gcc gcg atg ctc ccc ttc ctt ggc gac ttc atg agc ctg acg ggt gca ctc    1367 agc acc ttt ccc ctg aca ttc gtt ctt gca aat cac atg tac ctc acg gtg    1418 aag cag aac aag atg tcc atc ttc agg aaa tgc tgg cac tgg ctg aac gtt    1469 gtt ggc ttc agc tgc ttg tcc gtc gca gct gcg gtt gct gcg gtg agg cta    1520 atc acg gtc gac tac agt aca tac cat ttg ttt gct gat atg                1562 tgaggctgga aagtgcaagc atgcagccct ggatcagctg taaattcgtc ctcttctttt      1622
ttattttttt ggttagggga tgcatgtagg tcgatagaat gatggagatt gcaataaata      1682
atttggctaa aatgttgtcc agatttggtt gtttgaggtg caagatgttt gcctcaaaac      1742
gtaccgctat ggttcacttt ttaagaactg tactgctacc tctgtttgcg gagattttg       1802 tctgcaggca tgcaggatga atattattca agtgctctaa acgaggatcc gggtaccatg      1862
g                                                                      1863
```

<210> SEQ ID NO 2
<211> LENGTH: 473
<212> TYPE: PRT
<213> ORGANISM: Oryza sativa L.
<220> FEATURE:
<221> NAME/KEY: CDS
<222> LOCATION: 1..473
<300> PUBLICATION INFORMATION:
<308> DATABASE ACCESSION NUMBER: BAA93437
<309> DATABASE ENTRY DATE: 1999-01-25

<400> SEQUENCE: 2

```
Met Asp Gln His Gln Leu Asp Glu Glu Asn Gln Arg Ala Ala Leu Phe
  1               5                  10                  15

His Ser Ser Ala Pro Ser Ser Ser Leu Gly Ala Asp Gly Glu Glu Glu
             20                  25                  30

Arg Glu Thr Val Pro Leu Leu Ser Cys Lys Met Ala Asp Asp Lys Ser
         35                  40                  45

Asp Thr Val Gln Val Ser Glu Asp Thr Ala His Gln Ile Ser Ile Asp
     50                  55                  60

Pro Trp Tyr Gln Val Gly Phe Ile Leu Thr Thr Gly Val Asn Ser Ala
 65                  70                  75                  80

Tyr Val Leu Gly Tyr Ser Ala Ser Ile Met Val Pro Leu Gly Trp Ile
                 85                  90                  95

Gly Gly Thr Cys Gly Leu Ile Leu Ala Ala Ile Ser Met Tyr Ala
            100                 105                 110

Asn Ala Leu Leu Ala His Leu His Glu Val Gly Gly Lys Arg His Ile
        115                 120                 125

Arg Tyr Arg Asp Leu Ala Gly His Ile Tyr Gly Arg Lys Met Tyr Ser
    130                 135                 140

Leu Thr Trp Ala Leu Gln Tyr Val Asn Leu Phe Met Ile Asn Thr Gly
145                 150                 155                 160

Leu Ile Ile Leu Ala Gly Gln Ala Leu Lys Ala Ile Tyr Val Leu Phe
                165                 170                 175

Arg Asp Asp Gly Val Leu Lys Leu Pro Tyr Cys Ile Ala Leu Ser Gly
            180                 185                 190
```

```
                                  -continued

Phe Val Cys Ala Leu Phe Ala Phe Gly Ile Pro Tyr Leu Ser Ala Leu
        195                 200                 205

Arg Ile Trp Leu Gly Leu Ser Thr Val Phe Ser Leu Ile Tyr Ile Met
        210                 215                 220

Ile Ala Phe Val Met Ser Leu Arg Asp Gly Ile Thr Thr Pro Ala Lys
225                     230                 235                 240

Asp Tyr Thr Ile Pro Gly Ser His Ser Asp Arg Ile Phe Thr Thr Ile
                245                 250                 255

Gly Ala Val Ala Asn Leu Val Phe Ala Tyr Asn Thr Gly Met Leu Pro
                260                 265                 270

Glu Ile Gln Ala Thr Ile Arg Pro Pro Val Val Lys Asn Met Glu Lys
        275                 280                 285

Ala Leu Trp Phe Gln Phe Thr Val Gly Ser Leu Pro Leu Tyr Ala Val
        290                 295                 300

Thr Phe Met Gly Tyr Trp Ala Tyr Gly Ser Ser Thr Ser Ser Tyr Leu
305                 310                 315                 320

Leu Asn Ser Val Lys Gly Pro Ile Trp Ile Lys Thr Val Ala Asn Leu
                325                 330                 335

Ser Ala Phe Leu Gln Thr Val Ile Ala Leu His Ile Phe Ala Ser Pro
                340                 345                 350

Met Tyr Glu Phe Leu Asp Thr Arg Phe Gly Ser Gly His Gly Gly Pro
            355                 360                 365

Phe Ala Ile His Asn Ile Met Phe Arg Val Gly Val Arg Gly Gly Tyr
        370                 375                 380

Leu Thr Val Asn Thr Leu Val Ala Ala Met Leu Pro Phe Leu Gly Asp
385                 390                 395                 400

Phe Met Ser Leu Thr Gly Ala Leu Ser Thr Phe Pro Leu Thr Phe Val
                405                 410                 415

Leu Ala Asn His Met Tyr Leu Thr Val Lys Gln Asn Lys Met Ser Ile
                420                 425                 430

Phe Arg Lys Cys Trp His Trp Leu Asn Val Val Gly Phe Ser Cys Leu
            435                 440                 445

Ser Val Ala Ala Ala Val Ala Ala Val Arg Leu Ile Thr Val Asp Tyr
    450                 455                 460

Ser Thr Tyr His Leu Phe Ala Asp Met
465                 470
```

US 6,423,838 B1

GENE FOR PROLINE TRANSPORTER IN RICE

BACKGROUND OF THE INVENTION

The present invention relates to a gene for proline transporter in rice.

It is known that some plants, including halophytes, when they are under salt stress, accumulate proline in their bodies. It is considered that the proline accumulated serves as a compatible osmolyte, regulating the intracellular osmotic pressure and keeping water in the plant body. In plants, proline is synthesized from glutamic acid by two reactions catalyzed by two enzymes, namely $\Delta^1$-pyrroline-5-carboxylate (P5C) synthetase (P5CS) and $\Delta^1$-pyrroline-5-carboxylate reductase (P5CR), respectively.

When such plants undergo water stress (state in which water absorption is difficult), such as salt stress or water deficit, the levels of P5CS activity and P5CS gene expression increase. In that case, the levels of P5CR activity and P5CR gene expression remain almost constant and are low. This indicates that P5CS is a rate-limiting factor in the proline synthesis under water stress (Yoshiba et al., Plant J. 7:751–760 (1995)).

Kishor et al. succeeded in increasing the salt tolerance of tobacco by introducing the P5CS gene of mothbean thereinto to thereby cause overexpression of that gene, indicating that gene manipulation involving the P5CS gene is effective in producing salt tolerant crop plants (Kishor et al., Plant Physiol. 108:1387–1394 (1995)).

Not only the proline synthesis but also proline transport is involved in the accumulation of proline under water stress. As regards the proline transport, two proline transporter genes have been cloned from *Arabidopsis thaliana* and three from tomato. The transporters, unlike other amino acid permeases, transport proline alone selectively.

Upon amino acid sequence comparison, the two Arabidopsis proline transporter genes are shown to be very close to each other. They differ, however, in the mode of gene expression from each other. One is the Arabidopsis proline transporter 1 (AtProT1) gene, which is expressed constantly at a low level throughout tissues, and the other is the Arabidopsis proline transporter 2 (AtProT2) gene, which is scarcely expressed under normal growth conditions but whose expression is swiftly and intensely induced under salt stress conditions. Therefore, the latter gene is considered to be a transporter gene prepared exclusively for water stress and serving to transport proline as a compatible osmolyte (Rentsch et al., The Plant Cell 8:1437–1446 (1996)).

Among the three proline transporter genes cloned from tomato, the proline transporter 1 (LeProT1) gene has been analyzed to a good extent with respect to its function and it is known that it is intensely expressed in the process of pollen maturation and LeProT1 transports proline to and cause accumulation thereof in pollen. It is a characteristic feature of LeProT1 that it transports not only proline but also glycine betaine and like compatible osmolytes induced by water stress. At present, no report is available of the functions of the proline transporter 2 (LeProT2) and proline transporter 3 (LeProT3). However, since the genes encoding them belong to the same gene family as that to which the LeProT1 belongs, they are considered to be involved in amino acid transport to pollen and/or in stress-responding transport, like AtProT2 (Schwacke et al., The Plant Cell 11:377–391 (1999)).

SUMMARY OF THE INVENTION

For proline accumulation under water stress, proline synthesis and transport of the proline synthesized are both important. For plants to cope with rapid environmental changes such as drought and/or salt stress, it is effective to prompt proline synthesis as far as possible and transport proline to tissues requiring it. If, for such purposes, the P5CS gene can be manipulated to realize overexpression thereof and proline synthesis activation and, further the proline transporter gene or genes can be manipulated to realize overexpression thereof for transportation of the proline synthesized to tissues requiring the same, it will become possible to breed rice and other useful crop plants showing synergistic action and further having high salt tolerance and drought resistance. It is estimated that the proportion of saline soils resulting from drought and semidrought will increase more and more in the future as a result of destruction of the natural environment. Thus, breeding such tolerant or resistant crop plants as mentioned above plays an important role in solving the global food problem.

As far as the proline transporter genes in plants are concerned, only the corresponding cDNAs have so far been isolated from *Arabidopsis thaliana* and tomato. None has been isolated from monocots. Under such circumstances, the present invention provides a proline transporter gene in rice, which is a monocot. The present invention, by which a monocot proline transporter gene, which is quite unknown in the art, has been isolated, can be said to have achieved a novel technological advancement.

The present invention, which has been made with attention paid to the importance of such a rice proline transporter, has succeeded in solving a novel technical problem of controlling such transporter by gene manipulation. Namely, the present inventors newly raised the above technical problem so far not recognized in the art and approached the problem from various angles. Thus, they made intensive investigations in an attempt to isolate a relevant gene from rice seedling tissues and, as a result, successfully isolated a cDNA coding for the full length of a rice proline transporter gene from a cDNA library prepared by reverse transcription of mRNA.

BRIEF DESCRIPTION OF THE DRAWINGS

FIG. 1 comparatively shows the hydropathy plots deduced from the amino acid sequences of the rice proline transporter and the two Arabidopsis proline transporters. Thus.

FIG. 2 shows the results of expression analysis of the rice proline transporter gene. Thus.

DESCRIPTION OF THE PREFERRED EMBODIMENT

Figure 1A:
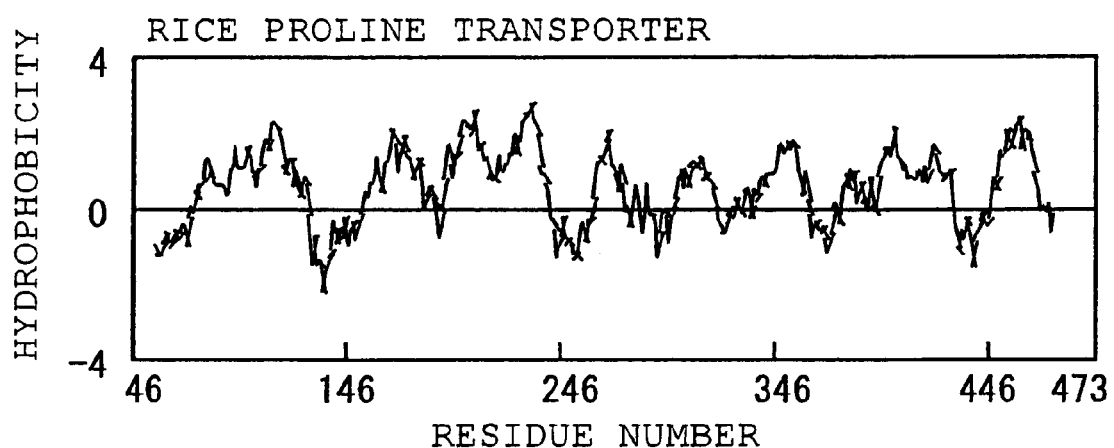
FIG. 1A shows the plot pattern of the transporter of the present invention and FIG. 1B, and FIG. 1C show the plot patterns of the two Arabidopsis proline transporters AtProT1 and AtProT2.

The present invention relates to a rice proline transporter gene (cDNA), and the DNA sequence thereof is as shown in the sequence listing under SEQ ID NO. 1. This gene was found to be comprised of 1,863 base pairs and have one open reading frame and the sequence AATAAA for polyadenylation at the 3' terminus. The present invention also includes a phage containing the rice proline transporter gene (cDNA) as well as a plasmid derived therefrom.

In practicing the present invention, mRNA is first extracted from rice seedlings and cDNA is prepared using the mRNA extracted. This cDNA is joined to a vector, which is a plasmid or phage, and then introduced into a host microorganism for recombinant DNA preparation. From among the transformed microorganisms harboring this recombinant DNA introduced therein, a desired transformant is selected by conventional screening, for example using the Arabidopsis-derived AtProT1 and/or AtProT2 gene as a probe. The desired plasmid is isolated from the transformant obtained and, if necessary, cloned by cleavage with an appropriate restriction enzyme or enzymes and subcloning in a plasmid vector. This cloned DNA is used for preparing a transformant, which is then cultivated, whereby the rice proline transporter can be recovered in large quantities from the culture.

The rice proline transporter gene prepared according to the present invention can be ligated to the downstream end of a potent promoter or a promoter enabling specific expression in leaf or roots and joined to a plasmid. The resulting recombinant plasmid can be introduced into cells of rice or some other useful plant in the conventional manner, for example by the technique of electroporation or Agrobacterium transfection, for regenerating plant bodies from the thus-transformed cells. In this manner, the rice or useful plant, which produces the rice proline transporter in excess, transports proline to and causes accumulation thereof in the plant body or a specific tissue or tissues, such as leaf, roots, etc. When the gene is ligated to the downstream end of a promoter enabling specific expression under stress conditions for joining to a plasmid and the resulting recombinant plasmid is introduced into cells of rice or some other useful plant in the conventional manner, for example by the electroporation or Agrobacterium transfection technique,. the rice or useful plant regenerated from these cells produces the rice proline transporter in excess specifically under stress conditions, which transfers and accumulates proline.

The following example illustrates the present invention in further detail. The example is, however, by no means limitative of the scope of the invention. In the following example, unless otherwise specified, the respective procedures were carried out essentially as described in Sambrook et al.: Molecular Cloning, Cold Spring Harbor Lab. (1989).

EMBODIMENT

First, a cDNA library was constructed from seedlings of the rice cultivar "Akibare". Thus, total RNA was extracted from 10 g of seedlings two weeks after germination by the guanidine thiocyanate/CsCl method. mRNA was separated from the total RNA extracted, using Oligo (dT) Latex (Takara, Kusatsu, Japan). The yield of mRNA was about 1.2% based on the total RNA. cDNA synthesis from the mRNA was carried out using a commercial cDNA synthesis kit (Stratagene, La Jolla, Calif., USA). The cDNA synthesized was inserted into λ ZAP II (Stratagene, La Jolla, Calif., USA), a λ phage vector, followed by infection of *Escherichia coli* with the resulting recombinant, to give a cDNA library.

Then, about six positive clones were obtained by the plaque hybridization method using the previously isolated AtProT1 and AtProT2 gene cDNAs as probes. These clones were subcloned in Bluescript and all of them were examined for their length by restriction enzyme treatment and the 5' and 3' termini were partly sequenced by the cycle sequencing method. In this way, a clone probably containing the full length of a proline transporter gene cDNA was obtained. From this clone, clones differing by about 300 bp were obtained using a DNA deletion kit. Plasmid DNAs were extracted from these clones and submitted to full-length cDNA sequencing by the cycle sequencing method.

Figure 1B:
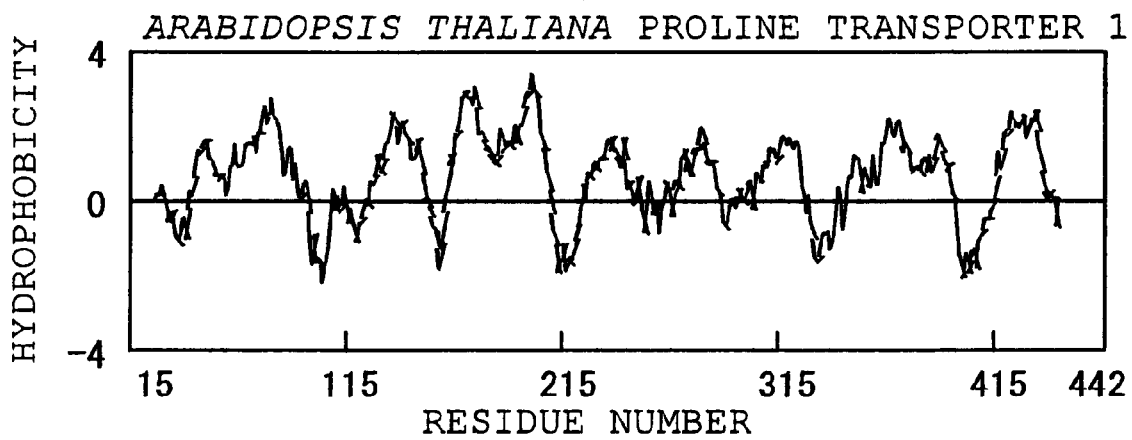
Figure 1C:
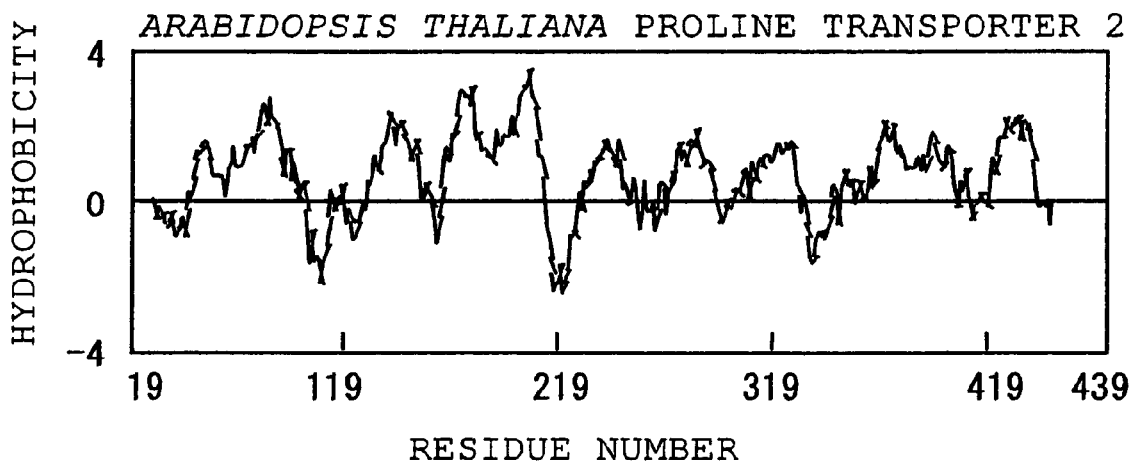

Upon homology analysis, the thus-sequenced cDNA showed high homology, namely 68.8% homology, on the amino acid level, with the AtProT1 gene previously isolated and expressed in all tissues of *Arabidopsis thaliana* and 67.8% homology, on the amino acid level, with the AtProT2 gene expressed specifically under salt stress. In addition, the proline transporter protein was compared with the two Arabidopsis proline transporter AtProT1 and AtProT2 proteins by hydropathy plotting by which the transmembrane domain, in the cell membrane, of the proline transporter protein can be predicted. The results of such comparison are shown in FIG. 1. FIG. 1 shows the hydropathy plots predicting the transmembrane domain, of each proline transporter protein, the abscissa denoting the amino acid residue number and the ordinate denoting the hydrophobicity. FIG. 1A shows the pattern of the plots of the transporter of the present invention and FIG. 1B and FIG. 1C show the plot patterns for the two Arabidopsis proline transporters AtProT1 and AtProT2, respectively. As shown in FIG. 1, the plot patterns are very similar to one another, hence the cDNA sequenced in the above manner was identified as a proline transporter gene in rice.

Figure 2A:
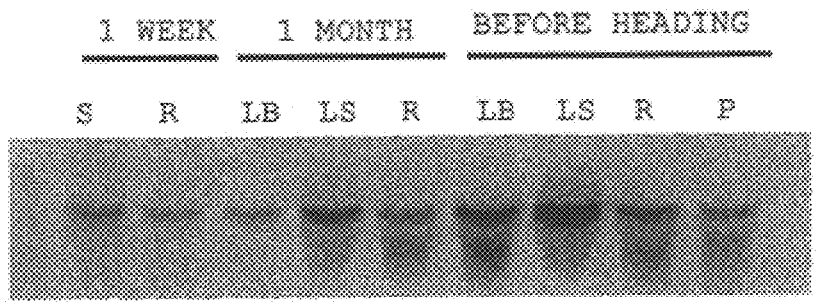
FIG. 2A shows the levels of expression of the gene in several organs of rice throughout plant growth and FIG. 2B and FIG. 2C show the levels of expression under different salt stress conditions.
Figure 2B:
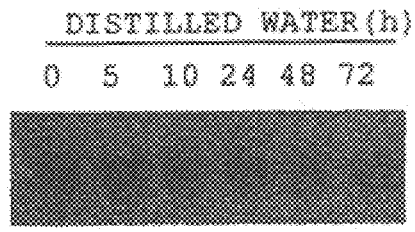
Figure 2C:
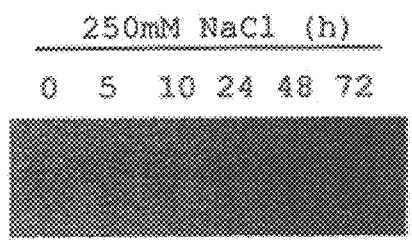

Further, using this cDNA as a probe, the levels of gene expression were checked by the Northern analysis method. FIG. 2A shows the results of such examination of the rice proline transporter gene expression in several organs of rice at several growth stages, namely at one week of age, at one month of age, and before heading. In one-week-old rice, the leaf blade, and stem were examined. In one-month-old rice, the leaf blade, leaf sheath and stem were examined. Before heading, the leaf, sheath, root and young panicle were examined. As is evident from the results shown, the gene of the present invention was expressed in all the tissues examined, in particular abundantly in the leaf sheath, stem and mature leaf blade having a well-developed vascular system. FIG. 2B and FIG. 2C show the results of rice proline transporter gene expression analysis under salt stress conditions. FIG. 2B shows, as a function of time, the levels of gene expression in a state in which the root was immersed in distilled water. FIG. 2C shows, as a function of time, the levels of gene expression in a state in which the root was immersed in a 250 mM NaCl solution, with no increases in expression level as compared with hour 0, like under distilled water treatment. It was thus revealed that the expression of the gene of the present invention is not induced by high salt treatment. Based on these results, the gene of the present invention was estimated to be equivalent in function to the AtProT1 gene which is expressed in all tissues of *Arabidopsis thaliana*.

As described hereinabove, it was revealed that the gene of the present invention encodes a proline transporter. The nucleotide sequence revealed and the corresponding amino acid sequence are shown in the sequence listing under SEQ ID NO. 1. The structure of such rice proline transporter gene has been determined for the first time by the present invention.

Therefore, by enhancing the gene of the present invention in plant, it is possible to cause rapid transport and accumulation of proline to thereby provide the plant with salt tolerance or drought resistance. Furthermore, by breeding rice or other useful crop plants with the gene of the invention and the rice $\Delta^1$-pyrroline-5-carboxylate synthetase gene previously proposed by the present inventors in Japanese Unexamined Patent Publication H10-57069 introduced therein together with a promoter capable of promoting gene expression in a severe environment such as a high salt condition, it can be expected that the transformed rice or other plants might be cultivated even in saline soils containing accumulated salts or in desert soils and the food production might be increased accordingly. It is also expected that the increases in population in developing countries might be coped with thereby.

Paying attention to the importance of the proline transporter in rice, the present inventors posed a novel technical problem of controlling this transporter by gene manipulation and successfully solved the problem. If the gene coding for P5CS, which is a rate-limiting factor in proline synthesis can be manipulated to realize overexpression thereof and proline synthesis activation and, further the proline transporter gene or genes can be manipulated to realize overexpression thereof for rapid transportation of the proline synthesized to tissues requiring the same, it will become possible to breed rice and other useful crop plants showing synergistic action and further having high salt tolerance and drought resistance. It is estimated that the proportion of saline soils resulting from drought and semidrought will increase more and more in the future as a result of destruction of the natural environment. Thus, breeding such tolerant crop plants as mentioned above plays an important role in solving the global food problem.

What is claimed is:

1. An isolated rice proline transporter nucleic acid which comprises SEQ ID NO: 1 or encodes SEQ ID NO: 2.

2. The isolated rice proline transporter nucleic acid according to claim 1, comprising SEQ ID NO: 1 and encoding SEQ ID NO: 2.

3. A phage vector or plasmid resulting from ligation of a vector fragment with a rice proline transporter nucleic acid comprising SEQ ID NO: 1 or encoding SEQ ID NO: 2.

4. The phage vector or plasmid according to claim 3, wherein the rice proline transporter nucleic acid comprises SEQ ID NO: 1 and encodes SEQ ID NO: 2.

5. A probe for identifying or isolating a rice proline transporter nucleic acid, comprising a rice proline transporter nucleic acid comprising SEQ ID NO: 1 or encoding SEQ ID NO: 2.

6. The probe according to claim 5, wherein the rice proline transporter comprises SEQ ID NO: 1 and encodes SEQ ID NO: 2.

* * * * *